(12) United States Patent
Navickas et al.

(10) Patent No.: US 10,428,361 B2
(45) Date of Patent: Oct. 1, 2019

(54) BIOCATALYTIC PRODUCTION OF L-FUCOSE

(71) Applicant: BASF SE, Ludwigshafen (DE)

(72) Inventors: Vaidotas Navickas, Mannheim (DE);
Michael Breuer, Darmstadt (DE);
Michael Puhl, Hirschberg (DE);
Melanie Weingarten, Ratzeburg (DE);
Kai-Uwe Baldenius, Mannheim (DE);
Wolfgang Siegel, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/559,962

(22) PCT Filed: Feb. 19, 2016

(86) PCT No.: PCT/EP2016/053591
§ 371 (c)(1),
(2) Date: Sep. 20, 2017

(87) PCT Pub. No.: WO2016/150629
PCT Pub. Date: Sep. 29, 2016

(65) Prior Publication Data
US 2018/0073047 A1    Mar. 15, 2018

(30) Foreign Application Priority Data
Mar. 26, 2015 (EP) .................................... 15160945

(51) Int. Cl.
*C12P 19/02* (2006.01)
*C12N 9/04* (2006.01)
*C12N 9/08* (2006.01)

(52) U.S. Cl.
CPC ............ *C12P 19/02* (2013.01); *C12N 9/0006* (2013.01); *C12N 9/0065* (2013.01); *C12Y 101/03009* (2013.01); *C12Y 111/01006* (2013.01); *C12Y 111/01007* (2013.01)

(58) Field of Classification Search
None
See application file for complete search history.

(56) References Cited

U.S. PATENT DOCUMENTS

| 7,575,910 | B2 | 8/2009 | Suzuki et al. |
| 8,642,297 | B2 | 2/2014 | Wymer et al. |
| 2014/0141440 | A1 | 5/2014 | Zelder et al. |
| 2015/0211036 | A1 | 7/2015 | Naesby et al. |
| 2015/0275248 | A1 | 10/2015 | Zelder et al. |
| 2016/0046645 | A1 | 2/2016 | Ernst et al. |
| 2016/0083328 | A1 | 3/2016 | Demming et al. |
| 2016/0168597 | A1 | 6/2016 | Breuer et al. |
| 2016/0176803 | A1 | 6/2016 | Weingarten et al. |
| 2016/0194272 | A1 | 7/2016 | Weingarten et al. |
| 2016/0194273 | A1 | 7/2016 | Weingarten et al. |
| 2016/0201093 | A1 | 7/2016 | Breuer et al. |
| 2016/0237170 | A1 | 8/2016 | Rittig et al. |
| 2017/0145451 | A1 | 5/2017 | Baldenius et al. |
| 2017/0217884 | A1 | 8/2017 | Schäfer et al. |
| 2017/0233338 | A1 | 8/2017 | Schäfer et al. |
| 2017/0233780 | A1 | 8/2017 | Breuer et al. |
| 2017/0247726 | A1 | 8/2017 | Budde et al. |
| 2017/0260519 | A1 | 9/2017 | Hage et al. |
| 2017/0283840 | A1 | 10/2017 | Braun et al. |
| 2017/0305849 | A1 | 10/2017 | Schäfer et al. |
| 2017/0305850 | A1 | 10/2017 | Schäfer et al. |
| 2018/0044438 | A1 | 2/2018 | Rittig et al. |

FOREIGN PATENT DOCUMENTS

| WO | WO-2005087941 A1 | 9/2005 |
| WO | WO-2010022244 A1 | 2/2010 |
| WO | WO-2012034996 A1 | 3/2012 |
| WO | WO-2014/030096 A2 | 2/2014 |
| WO | WO-2014/080316 A1 | 5/2014 |
| WO | WO-2014/154806 A1 | 10/2014 |
| WO | WO-2014/154814 A1 | 10/2014 |
| WO | WO-2014/155214 A1 | 10/2014 |
| WO | WO-2014/180871 A1 | 11/2014 |
| WO | WO-2015/014644 A1 | 2/2015 |
| WO | WO-2015/014651 A1 | 2/2015 |
| WO | WO-2015/049345 A1 | 4/2015 |
| WO | WO-2015/092575 A1 | 6/2015 |
| WO | WO-2016/001362 A1 | 1/2016 |
| WO | WO-2016/023732 A1 | 2/2016 |
| WO | WO-2016/023772 A1 | 2/2016 |

(Continued)

OTHER PUBLICATIONS

R.L. Root et al. "Enzymatic Synthesis of Unusual Sugars: Galactose Oxidase Catalzed Stereospecific Oxidation of Polyols", J. Am. Chem. Soc. 107(10): 2997-2999 (Year: 1985).*
International Search Report for PCT/EP2016/053591 dated Apr. 15, 2016.
Written Opinion of the International Searching Authority for PCT/EP2016/053591 dated Apr. 15, 2016.
U.S. Appl. No. 15/510,268, Puhl et al.
U.S. Appl. No. 15/509,993, Navickas et al.
U.S. Appl. No. 15/552,522, Rittig et al.
International Preliminary Report on Patentability dated Sep. 27, 2017 in International Application No. PCT/EP2016/053591 (7 pages) with an English translation (7 pages).

(Continued)

*Primary Examiner* — Rebecca E Prouty
(74) *Attorney, Agent, or Firm* — Drinker Biddle & Reath LLP

(57) ABSTRACT

The present invention relates to biocatalytic methods, comprising purely enzymatic, mixed enzymatic-fermentative and purely fermentative methods, for the direct single-step conversion of L-fucitol to L-fucose, in order to easily obtain L-fucose at high amounts and levels of purity. Suitable recombinant microorganisms and fungi are further disclosed and also the use thereof in said method for the single-step conversion to L-fucose.

22 Claims, 2 Drawing Sheets

(56) References Cited

FOREIGN PATENT DOCUMENTS

| WO | WO-2016/037720 A1 | 3/2016 |
|---|---|---|
| WO | WO-2016/037785 A1 | 3/2016 |
| WO | WO-2016/038192 A1 | 3/2016 |
| WO | WO-2016/050690 A1 | 4/2016 |
| WO | WO-2016/050816 A2 | 4/2016 |
| WO | WO-2016/050817 A1 | 4/2016 |
| WO | WO-2016/050818 A1 | 4/2016 |
| WO | WO-2016/050819 A1 | 4/2016 |
| WO | WO-2016/050861 A1 | 4/2016 |
| WO | WO-2016/050909 A1 | 4/2016 |
| WO | WO-2016/135030 A1 | 9/2016 |
| WO | WO-2016/135031 A1 | 9/2016 |
| WO | WO-2016/150629 A1 | 9/2016 |

OTHER PUBLICATIONS

Parikka et al., "Oxidation of methyl α-D-galactopyranoside by galactose oxidase: products formed and optimization of reaction conditions for production of aldehyde," Carbohydrate Research, vol. 344, pp. 14-20, 2009.

* cited by examiner

Influence of H$_2$O$_2$ on conversion of L-fucitol to L-fucose by GO

Influence of L-fucose on conversion of L-fucitol by GO

BIOCATALYTIC PRODUCTION OF L-FUCOSE

CROSS-REFERENCE TO RELATED APPLICATIONS

This application is a national stage application (under 35 U.S.C. § 371) of PCT/EP2016/053591, filed Feb. 19, 2016, which claims benefit of European Application No. 15160945.0, filed Mar. 26, 2015, both of which are incorporated herein by reference in their entirety.

TECHNICAL FIELD

The present invention relates to methods for the biocatalytic, i.e. enzymatic and/or fermentative, production of L-fucose from L-fucitol. The present invention further discloses enzymes, in particular a galactose oxidase, which are suitable for the biocatalytic production of L-fucose from L-fucitol. Recombinant microorganisms and fungi are furthermore disclosed which bear the nucleic acid sequences, expressible as transgenes, required for the enzymes for the production of L-fucose from L-fucitol, and can express this functionally, and also the use of these microorganisms or fungi in the methods according to the present invention.

BACKGROUND OF THE INVENTION

Fucose occurs in two enantiomeric forms: L-fucose (also called isodulcitol) and D-fucose (CAS 3615-37-0). The L form is widespread in nature. L-fucose is a fundamental molecule for use in research and development and a characteristic component of glycan structures. Scientific investigations in the field of fucosylated substances have shown, among other things, that these are of outstanding importance in embryonic development and are involved in the immune response of the organism.

L-fucose is found, inter alia, in human breast milk. Human breast milk plays an important role in healthy child development. The substances present therein, particularly the oligosaccharides (human milk oligosaccharides (HMO)), are one of the integral main components of breast milk and have a core structure which has a lactose unit at the reducing end and is elongated by N-acetyllactosamine units in a branched or chain-like manner. The structural variability is extended, inter alia, by fucosyl modifications at the end positions. With regard to the health and developmental effect, the biological function of the HMOs is the subject of numerous studies, but this requires the technical purity of the compounds in sufficient amounts. At present, L-fucose is provided either by direct extraction from natural sources or by chemical modification of monosaccharides (for a summary, see P. T. Vanhooren et al. J. Chem. Technol. Biotechnol. 74, 479 (1999) and sources cited therein). The laborious extraction from breast milk is currently the most widely used method. Although biotechnological production processes for HMOs have been described (see Han et al., *Biotechnol. Adv.* 2012, 30, 1268-1278), the corresponding HMOs are frequently not obtainable at a reasonable price.

L-fucose and L-fucose-containing substances are the subject of ongoing research. L-fucose itself and fucosylated substrates are important starting materials in the chemical and pharmaceutical industry and also useful in the production of cosmetics and neutraceuticals. Therefore, there is a continuing need for innovative production processes for the production of L-fucose on an industrial scale.

Biotechnological methods have been proposed to obtain L-fucose. For instance, WO 2012/034996 A1 teaches a method for producing L-fucose using an isolated microorganism of the family Enterobacteriaceae (deposited as DSM 22227), which has a specific 16S rRNA according to SEQ ID NO:1, for the production of L-fucose by fermentation. However, the L-fucose is obtained as a non-purified mixture only after time-consuming fermentation, which is why laborious further purification steps are necessary to obtain L-fucose. U.S. Pat. No. 8,642,297 B2 postulates, inter alia, a generic fermentation process which is intended to produce L-fucose using a recombinant mannitol-1-dehydrogenase from *Apium graveolens*. However, neither a specific working example nor an example is disclosed. Furthermore, no alternative enzyme is disclosed which could be used for the reaction. WO 2005/087941 A1 discloses a combined fermentative-enzymatic method for providing L-fucose. For this purpose, L-fuculose is first produced from L-fucitol by using a dehydrogenase of an *Acetobacterium*. This must then be synthesized in a further step to give L-fucose.

There is therefore still a great need to be able to produce L-fucose in sufficient purity economically in as few steps as possible in a process which can be used industrially.

SUMMARY OF THE INVENTION

The object of the present invention is therefore to provide a method for the biotechnological production of L-fucose and also enzymes suitable for this purpose, and recombinant microorganisms and fungi, wherein L-fucose may be obtained directly from L-fucitol in a single-step reaction on an industrial scale.

The present invention achieves this object by providing a method using L-fucitol and galactose oxidase and also optionally further enzymes selected from a peroxidase and/or a catalase, whereby the conversion of L-fucitol to L-fucose may be carried out in a single-step reaction and high yields can be achieved in this case. Enzymes suitable for this purpose are also disclosed. Finally, a recombinant microorganism or fungus is disclosed, which can produce relevant enzymes for the synthetic route disclosed, and also use thereof.

Aspects and embodiments of the present invention will become apparent from the following detailed description and the examples, the figures, and the appended patent claims.

DETAILED DESCRIPTION

Definitions

Figure 1:
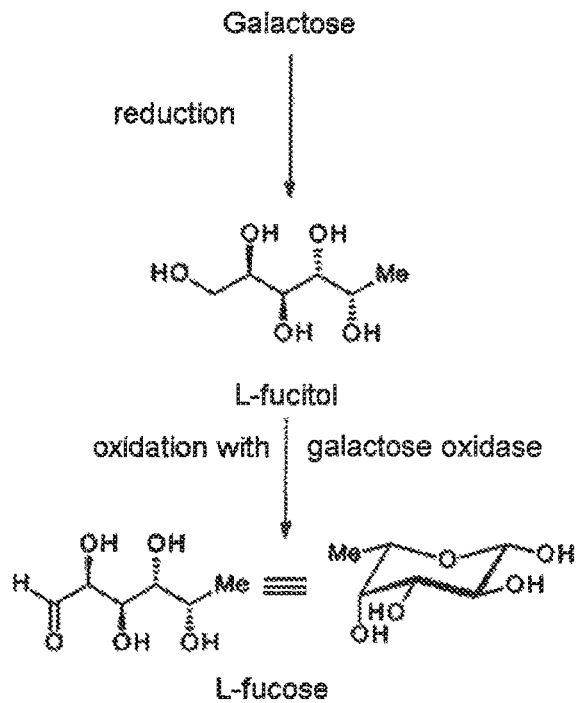
FIG. 1 (FIG. 1) shows the reaction pathway of galactose via L-fucitol to give L-fucose, wherein the step of oxidation of L-fucitol is effected by a galactose oxidase.

The terms protein, polypeptide and enzyme are used interchangeably due to the constant enzymatic function of the polypeptides disclosed herein.

The terms biocatalytic or biocatalysis, as used herein, refer to a reaction and acceleration or control of chemical reactions in which enzymes serve as biological catalysts. Biocatalysis can be performed either by the addition of isolated enzymes (enzymatic) or directly in living cells (here: fermentative).

The term recombinant microorganism or fungus, as used herein, refers to a microorganism or fungus which comprises a recombinant, i.e. (partially) artificial biomolecule of interest, wherein the biomolecule may be a nucleic acid sequence or a polypeptide sequence. In addition, the selected microorganism or fungal strain can carry mutations in its genome or on encapsulated plasmid DNA, as compared to an unmodified or to a wildtype strain, which does not relate to the nucleic acid sequence of the biomolecule of interest.

The term transgene as used herein refers to a nucleic acid molecule of a species which has been introduced either directly into the genome of another species or by means of a vector outside the genome but replicable in the other species. The organism thus modified is referred to herein as recombinant (see above).

The term descendant, as used herein, refers to the descendants of such an organism in the context of a recombinant microorganism or fungus according to the present disclosure, which originate from the organism of origin by natural reproductive processes of propagation, comprising sexual and asexual. It is known to those skilled in the art that, in the course of reproduction, mutations can naturally be introduced into the genome of an organism, whereby the descendants differ genomically from the parent organism, but can still be assigned to the same (sub)species. Such descendants modified by natural processes are therefore also encompassed by the term descendant according to the present disclosure.

The term vector as used herein refers to a transport vehicle for transferring a nucleic acid molecule into a cell, a microorganism or a fungus. Vectors may be, inter alia, plasmids, cosmids or modified viruses. Furthermore, the term vector is also intended to encompass means which are suitable for the direct introduction of a polypeptide into a cell or a microorganism.

The term "express in functional form" as used herein, refers to the ability of a recombinant microorganism or fungus to be able to translate one or more transgene(s) selected from the group consisting of a galactose oxidase, a catalase and a peroxidase, as defined above, to form a polypeptide which, under suitable reaction conditions, satisfies the enzymatic function of a galactose oxidase, a catalase or a peroxidase as set out above.

DETAILED DESCRIPTION OF THE INVENTION

In one aspect, the present invention provides a method for producing L-fucose comprising the following steps: (a) providing L-fucitol, (b) providing a galactose oxidase of the enzyme class EC 1.1.3.9 and optionally one or more further constituent(s), (c) oxidation of L-fucitol using a galactose oxidase and optionally the further constituent(s) and incubating the resulting mixture under conditions permitting the biocatalytic oxidation of L-fucitol to L-fucose, (d) optionally: isolating the synthesized L-fucose.

Galactose oxidase (EC 1.1.3.9) is a copper-dependent oxidase. It is often found in nature as an extracellular, monomeric enzyme which is secreted by many filamentous fungi. Galactose oxidases catalyze the oxidation of primary alcohols to the corresponding aldehydes while at the same time molecular oxygen is reduced to $H_2O_2$ (see Paukner, R. et al.; Galactose oxidase from *Fusarium oxysporum*—expression in *E. coil* and *P. pastoris* and biochemical characterization; *PLoS ONE*, 2014, 9, e100116/1). The activity of a galactose oxidase can be determined by methods known to those skilled in the art, wherein the release of hydrogen peroxide ($H_2O_2$) from reduction of oxygen ($O_2$) is quantified in the presence of a suitable substrate (particularly galactose). Alternatively, the lowering of the $O_2$ concentration is also a measure of the activity of a galactose oxidase.

In one embodiment of this aspect, the method comprises substep (b1) providing a recombinant microorganism or fungus for the recombinant expression of a galactose oxidase of the enzyme class EC 1.1.3.9, wherein the microorganism or fungus comprises a transgene which encodes a galactose oxidase from a fungus of the order of the Hypocreales, preferably selected from the genus *Fusarium*, in particular from the species *Fusarium oxysporum*, (b2) culturing the recombinant microorganism under conditions which permit the synthesis of the galactose oxidase, (b3) optionally: isolating the synthesized galactose oxidase. The preferred galactose oxidase from *Fusarium oxysporum* according to the present disclosure is a polypeptide comprising 681 amino acids (GenBank® deposit number: AHA90705.1). The corresponding nucleic acid sequence (2046 nucleotides including stop codon) of the coding sequence is accessible in the GenBank® as deposit number KF601698.1.

It is known to those skilled in the art that any enzyme of the enzyme class 1.1.3.9 defined by a comparable catalytic activity may be used in the method according to the present invention as long as the enzyme catalyzes the abovementioned function of the oxidation of primary alcohols to the corresponding aldehydes with simultaneous reduction of molecular oxygen to $H_2O_2$. It is likewise known to those skilled in the art that the reaction conditions may be varied depending on the enzyme used. Adjustments to the reaction and/or culture conditions may be made readily by those skilled in the art.

In one embodiment of this aspect, the one or more optional further constituent(s) is/are selected from the group consisting of peroxidases and/or catalases.

According to any aspect of the present invention, the biocatalytic recovery of L-fucose, starting from L-fucitol, is taught by the use of a galactose oxidase and optionally additionally a peroxidase and/or catalase. These biocatalytic reactions according to all aspects of the present invention can be carried out completely enzymatically, enzymatically and fermentatively, or exclusively by fermentation. Enzymatic in this context signifies the use of isolated and optionally purified and further modified enzymes. Fermentative in this context means the expression of one or more target enzyme(s) in a recombinant host organism under suitable reaction conditions which allow expression of the enzyme in functional form.

Due to the fact that the reaction of the conversion of L-fucitol to L-fucose using a galactose oxidase is an oxygen-dependent reaction, it is provided according to all aspects and embodiments of the present invention that the reactants always come into sufficient contact with oxygen. This oxygen input can be effected by means well known to those skilled in the art, such as, for example, aeration by gassing or aerating a culture or reaction batch.

As already mentioned, it is preferred if the one or more optional further constituent(s) is or are selected from the group consisting of peroxidases and/or catalases. Catalases catalyze the reaction of the overall equation: $2\ H_2O_2 \rightarrow O_2 + 2\ H_2O$ and therefore the by-product $H_2O_2$ is formed in the reaction of the galactose oxidase with L-fucitol. Peroxidases, such as horseradish peroxidases, are enzymes which catalyze the reduction of peroxides. The overall equation of the catalyzed reaction is also: $2\ H_2O_2 \rightarrow O_2 + 2\ H2O$. The substrate specificity of peroxidases can vary significantly. Horseradish peroxidase is a representative example of this enzyme class with a broad spectrum of donors and acceptors. For use in the present invention, any catalase or peroxidase is suitable which under suitable reaction conditions can catalyze the decomposition of $H_2O_2$ to oxygen and water.

Figure 3:
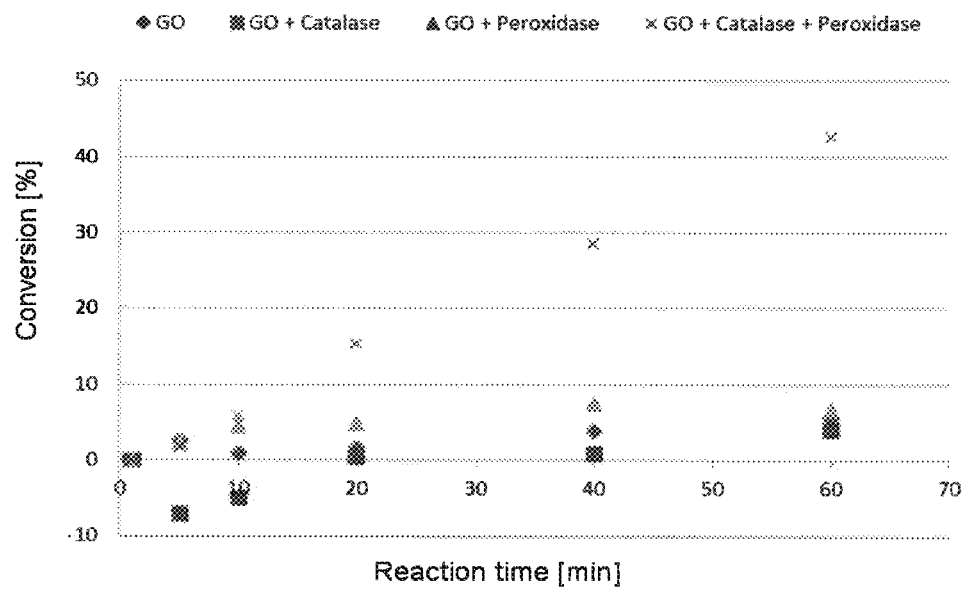
FIG. 3 (FIG. 3) shows the influence of $H_2O_2$ on the conversion of L-fucitol to L-fucose using a galactose oxidase over time.

It has been found that the addition of a peroxidase and/or a catalase advantageously influences the conversion of L-fucitol to L-fucose, since the $H_2O_2$ formed, inter alia, by the activity of the galactose oxidase is removed by the activity of these additional $H_2O_2$ detoxifying enzymes and the yield of L-fucose can therefore be increased. In one embodiment, either a catalase or a peroxidase is used in addition to the galactose oxidase. In a preferred embodiment, both a catalase and a peroxidase are used in addition to the galactose oxidase. The advantageous results of the latter embodiment are illustrated in FIG. 3.

In one embodiment, the peroxidase is selected from a peroxidase of the group consisting of the enzyme class EC 1.11.1.7, in particular from the peroxidase from horseradish (*Armoracia rusticana*). The horseradish peroxidase can either be purchased commercially (SIGMA-ALDRICH, e.g. product number: P8250), or can be recombinantly produced. The deposit numbers in the GenBank are X57564.1 for the mRNA of the nucleic acid sequence, or CAA40796.1 for the polypeptide sequence, for the enzyme from Armoracia rusticana.

In a further embodiment according to the first aspect of the present invention, the catalase is selected from a catalase of the group consisting of the enzyme class EC 1.11.1.6, in particular from the catalase from cattle (*Bos taurus*).

In one embodiment, the catalase is bovine liver catalase of the enzyme class EC 1.11.1,6 (source, for example, SIGMA ALDRICH, product number: C30), which is suitable for direct enzymatic conversion. For recombinant expression, the nucleic acid sequence of an exemplary bovine liver catalase is publicly available as NCBI reference sequence NM_001035386.2 (mRNA) and the corresponding translated polypeptide sequence is publicly accessible as NCBI reference sequence NP_001030463.1.

Likewise, for all aspects of the generation by fermentation of enzymes according to the present disclosure, galactose oxidase and/or peroxidase and/or catalase sequences with at least 80%, 81%, 82%, 83%, 84%, 85%, 86%, 87%, 88%, 89%, 90%, 91%, 92%, 93%, 94%, 95%, 96%, 97%, 98% or 99% sequence homology to the database sequences defined above are proposed, wherein the nucleic acid or polypeptide sequences may be codon-optimized or may contain targeted point mutations as long as the translated polypeptide still performs the function of the wild-type reference sequence. Such modifications for adapting the nucleic acid sequence and thus the polypeptide sequence of an enzyme are well known to those skilled in the art and are used, inter alia, to adapt the sequence to the codon usage of the recombinant host organism selected for expression, to optimize the enzyme stability or function, and also to increase the yield or lower the cytotoxicity of the enzyme product for the selected host organism.

Furthermore, the nucleic acid or polypeptide sequences of the present disclosure may carry labelling sequences ("tags") that permit the purification or detection of the translated polypeptide sequences, which are translated with the tag as fusion molecules. Such tags and their sequences and also methods for the modification of a target sequence are well-known to those skilled in the art and include sequences such as a streptavidin tag, polyhistidine tag, glutathione S-transferase tag, maltose binding protein tag, flash tag, tags which mediate secretion of the recombinant polypeptide into the culture supernatant, and the like.

In one embodiment of the present invention, the concentration of galactose oxidase in the mixture at the start of the incubation in step (c) according to the first aspect is in the range from 0.005 to 6.25 g/L, preferably in the range from 0.005 to 3.2 g/L, more preferably in the range from 0.005 to 0.5 g/L and especially preferably in the range from 0.005 to 0.05 g/L. It is known to those skilled in the art that the concentration of galactose oxidase used is dependent on the specific enzyme used and also the specific enzyme activity thereof. The enzyme activity may be specified in two possible units: (1) in units (1 enzyme unit)=1 μmol substrate $\min^{-1}$, or in SI units in katal (kat)=1 mol substrate $s^{-1}$. To those skilled in the art, the approximate calculation of the rate of an enzymatic reaction and thus also the enzyme activity is known by the Michaelis-Menten equation, so that the enzyme activity for an enzyme of interest can be readily determined in a suitable assay.

In another embodiment of the present invention, the concentration of peroxidase in the mixture at the start of the incubation in step (c) according to the first aspect is in the range from 0 to 0.5 g/L, preferably in the range from 0 to 0.3 g/L and more preferably in the range from 0 to 0.15 g/L.

In a further embodiment of the present invention, the concentration of catalase in the mixture at the start of the incubation in step (c) according to the first aspect is in the range from 0 to 0.4 g/L, preferably in the range from 0 to 0.2 g/L and more preferably in the range from 0 to 0.1 g/L.

In yet a further embodiment of the present invention, the concentration of L-fucitol in the mixture at the start of the incubation in step (c) according to the first aspect is in the range from 1 to 500 g/L, preferably in the range from 5 to 250 g/L, particularly preferably in the range from 20 to 125 g/L.

In one embodiment according to any aspect of the present invention, the recombinant microorganism or fungus is selected from the group consisting of *Escherichia coli* spp., preferably *E. coli* BL21, *E. coli* MG1655 or *E. coli* W3110 and descendants thereof, *Bacillus* spp., preferably *Bacillus licheniformis, Bacillus subitilis* or *Bacillus amyloliquefaciens*, and descendants thereof, Saccharomycetes, preferably of the order of the Saccharomycetales, more preferably of the family of the Saccharomycetaceae, more preferably of the genus *Komagataella*, preferably *Hansenula* or *Pichia* spp., particularly preferably *P. pastoris* and descendants thereof, *Kluyveromyces* spp., preferably *K. lactis*, and descendants thereof, *Aspergillus* spp., preferably *A. oryzae, A. nidulans* or *A. niger*, and descendants thereof, or *Trichoderma* spp., preferably *T. reesei* or *T. harzianum*, and descendants thereof, or a fungus of the phylum Ascomycota, preferably *Myceliopthora thermophila*, or a descendant thereof.

According to a further aspect of the present invention, a recombinant microorganism or fungus is provided, wherein the microorganism or fungus comprises a transgene which encodes a galactose oxidase from a fungus of the genus *Fusarium*, and further comprises a transgene selected from a peroxidase and/or a catalase as defined above, wherein the recombinant microorganism or fungus is selected from the group consisting of *Escherichia coli* spp., preferably *E. coli* BL21, *E. coli* MG1655 or *E. coli* W3110 and descendants thereof, *Bacillus* spp., preferably *Bacillus licheniformis, Bacillus subitilis* or *Bacillus amyloliquefaciens*, and descendants thereof, Saccharomycetes, preferably of the order of the *Saccharomycetales*, more preferably of the family of the Saccharomycetaceae, more preferably of the genus *Komagataella*, preferably *Hansenula* or *Pichia* spp., particularly preferably *P. pastoris* and descendants thereof, *Kluyveromyces* spp., preferably *K. lactis*, and descendants thereof, *Aspergillus* spp., preferably *A. oryzae, A. nidulans* or *A. niger*, and descendants thereof, or *Trichoderma* spp., preferably *T. reesei* or *T. harzianum*, and descendants thereof, or a fungus of the phylum Ascomycota, preferably *Myceliopthora thermophila*, or a descendant thereof, and wherein the recombinant microorganism or fungus can express the transgene(s) in functional form.

It is well known to those skilled in the art that the term "suitable (reaction) conditions" in the context of enzymes implies that the necessary substrates, buffer conditions, especially salt concentrations, optionally cofactors comprising, inter glia, prosthetic groups, coenzymes and metal ions, and pH and temperature conditions, which are indispensable or conducive to the activity of the corresponding enzyme, must be provided. In the case of the use of a galactose oxidase—an oxygen-dependent enzyme—this comprises, for example, aeration by gassing or aerating a culture or reaction batch. Since all enzymes of the present invention and the reaction catalyzed by them are well characterized, the determination of suitable reaction conditions is therefore within the capabilities of those skilled in this field.

In one embodiment, in addition to the transgene encoding a galactose oxidase, a further transgene encoding a catalase is present in the recombinant microorganism or fungus.

In another embodiment, in addition to the transgene encoding a galactose oxidase, a further transgene encoding a peroxidase is present in the recombinant microorganism or fungus.

In yet another embodiment, in addition to the transgene encoding a galactose oxidase, both a further transgene encoding a peroxidase and a transgene encoding a catalase are present in the recombinant microorganism or fungus.

The provision of the respective transgene, incorporation thereof into the recombinant microorganism or fungus, and also the selection of suitable culture and reaction conditions, which allow the transcription and translation of the respective transgene, are well known to those skilled in the art.

In one embodiment, the recombinant microorganism or fungus may be used by adding L-fucitol to the culture medium for the direct production of L-fucose from L-fucitol by fermentation, i.e. the recombinant microorganism or fungus is used directly to carry out the method described above. This embodiment permits the direct production of L-fucose, optionally followed by further purification steps, in the fermentation batch.

In one embodiment, the transgenes for the galactose oxidase and also the peroxidase and/or the catalase may be provided with a tag which permits the secretion of the translated polypeptides into the culture supernatant. This allows either the ready isolation of the enzymes from the culture supernatant or the direct implementation of the conversion of L-fucitol to L-fucitose after the addition of L-fucitol and the adjustment of the reaction conditions so that the secreted enzymes can fulfill their enzymatic function.

In another embodiment, the transgenes encoding a galactose oxidase, a peroxidase and/or a catalase are provided not in one, but in different recombinant microorganisms or fungi, and are expressed under suitable culture conditions and optionally purified. The method described herein can then be carried out in vitro or in vivo with the enzymes thus obtained after the addition of L-fucitol, so that L-fucose can be obtained from L-fucitol by providing suitable reaction conditions.

In a further aspect, the present invention provides for the use of a recombinant microorganism or fungus, wherein the microorganism or fungus comprises a transgene which encodes a galactose oxidase from a fungus of the genus *Fusarium*, as defined above, for recombinant expression of a galactose oxidase in a method as described above, wherein the recombinant microorganism or fungus is selected from the group consisting of *Escherichia coli* spp., preferably *E. coli* BL21, *E. coli* MG1655 or *E. coli* W3110 and descendants thereof, *Bacillus* spp., preferably *Bacillus licheniformis, Bacillus subitilis* or *Bacillus amyloliguefaciens*, and descendants thereof, Saccharomycetes, preferably of the order of the Saccharomycetales, more preferably of the family of the Saccharomycetaceae, more preferably of the genus *Komagataella*, preferably *Hansenula* or *Pichia* spp., particularly preferably *P. pastoris* and descendants thereof, *Kluyveromyces* spp., preferably *K. lactis*, and descendants thereof, *Aspergillus* spp., preferably *A. oryzae, A. nidulans* or *A. niger*, and descendants thereof, or *Trichoderma* spp., preferably *T. reesei* or *T. harzianum*, and descendants thereof, or a fungus of the phylum Ascomycota, preferably *Myceliopthora thermophila*, or a descendant thereof, and wherein the recombinant microorganism or fungus can express the transgene(s) in functional form.

In a further aspect, the present invention provides for the use of a galactose oxidase and at least one further enzyme selected from a peroxidase and/or a catalase, wherein the galactose oxidase and the peroxidase and/or the catalase is preferably obtained by a method comprising the following steps:

(a) providing a recombinant microorganism or fungus for the recombinant expression of a galactose oxidase and a peroxidase and/or a catalase, wherein the microorganism comprises a transgene which encodes a galactose oxidase from a fungus of the genus *Fusarium*, and comprises a further transgene which encodes a peroxidase and/or catalase, and wherein the recombinant microorganism or fungus is selected from the group consisting of *Escherichia coil* spp., preferably *E. coli* BL21, *E. coli* MG1655 or *E. coli* W3110 and descendants thereof, *Bacillus* spp., preferably *Bacillus licheniformis, Bacillus subitilis* or *Bacillus amyloliquefaciens*, and descendants thereof, Saccharomycetes, preferably of the order of the Saccharomycetales, more preferably of the family of the Saccharomycetaceae, more preferably of the genus *Komagataella*, preferably *Hansenula* or *Pichia* spp., particularly preferably *P. pastoris* and descendants thereof, *Kluyveromyces* spp., preferably *K. lactis*, and descendants thereof, *Aspergillus* spp., preferably *A. oryzae, A. nidulans* or *A. niger*, and descendants thereof, or *Trichoderma* spp., preferably *T. reesei* or *T. harzianum*, and descendants thereof, or a fungus of the phylum Ascomycota, preferably *Myceliopthora thermophila*, or a descendant thereof, or (b1) providing a first recombinant microorganism or fungus for the recombinant expression of a galactose oxidase, wherein the microorganism or fungus comprises a transgene encoding a galactose oxidase from a fungus of the genus *Fusarium*; and (b2) providing a second recombinant microorganism or fungus for the recombinant expression of a peroxidase, wherein the microorganism or fungus comprises a transgene encoding a peroxidase; and/or (b3) providing a third recombinant microorganism or fungus for the recombinant expression of a catalase, wherein the microorganism or fungus comprises a transgene encoding a catalase;

(c) culturing the recombinant microorganism under suitable conditions which permits the synthesis of the galactose oxidase and the peroxidase and/or the catalase, (d) optionally: isolating the synthesized galactose oxidase and the peroxidase and/or the catalase, for the biocatalytic conversion of L-fucitol to L-fucose, in a method according to the first aspect of the present invention.

For the peroxidase and/or the catalase, therefore, the above statement applies correspondingly in each case.

This aspect of the present invention is especially useful in order to provide, produce and optionally to isolate individually in one or more recombinant organism(s) all desired single enzymes for carrying out the biocatalytic conversion of L-fucitol to L-fucose, in order to subsequently carry out in vitro the conversion of L-fucitol to L-fucose enzymatically in a controlled manner.

EXAMPLES

The invention is now illustrated in more detail by the examples which are not to be regarded as limiting.

Example 1

Production of L-fucose by Biocatalytic Oxidation of L-fucitol with Galactose Oxidase in the Presence of Peroxidase and Catalase To a round-bottom three-necked flask (50 mL) was added a solution of L-fucitol (6.0 mL of aqueous solution comprising 600 mg of L-fucitol, CAS 13074-06-1, Santa Cruz Biotechnology), followed by addition of 1.2 mL of $K_2HPO_4/KH_2PO_4$ (1000 mM, pH=7.0) and of 0.095 mL of catalase (from bovine liver, SIGMA, 21 300 U/mg, 34 mg/mL), addition of 0.120 mL of peroxidase (from horseradish, 173 U/mg solid, SIGMA) and of 2.218 mL of galactose oxidase (38.4 mg/mL, 2708 U/mL). The resulting solution was purged at room temperature with $O_2$ until all the L-fucitol had been converted to L-fucose. The reaction was monitored by HPLC. The final product was isolated and analyzed by 1H- and 13C-NMR. The results are summarized in Table 1.

TABLE 1

| Reaction time [h] | Conversion [%] |
|---|---|
| 0 | — |
| 3.5 | 54.0 |
| 24 | 95.8 |
| 29 | 96.0 |

Example 2

Influence of Peroxidase and Catalase on the Biocatalytic Oxidation of L-fucitol

The following experiments were carried out on a 1.0 mL scale: Galactose oxidase (GO): To a 0.250 mL L-fucitol solution (100 mg/mL) were added 0.635 mL of water, followed by 0.050 mL of $K_2HPO_4/KH_2PO_4$ buffer solution, pH 7.0, 0.065 mL of galactose oxidase (2705 U/mL in 100 mM $K_3PO_4$ buffer, pH 6.0); GO+catalase: To a 0.250 mL L-fucitol solution (100 mg/mL) were added 0.631 mL of water, followed by 0.050 mL of $K_2HPO_4/KH_2PO_4$ buffer, pH 7.0, 0.004 mL of catalase in water (724 200 U/mL), 0.065 mL of galactose oxidase (2705 U/mL in 100 mM $K_3PO_4$ buffer, pH 6.0). GO+peroxidase: To a 0.250 mL L-fucitol solution (100 mg/mL) were added 0.630 mL of water, followed by 0.050 mL of $K_2HPO_4/KH_2PO_4$ buffer, pH 7.0, 0.005 mL of peroxidase in water (7500 U/mL), 0.065 mL of galactose oxidase (2705 U/mL in 100 mM $K_3PO_4$ buffer, pH 6.0); GO+peroxidase+catalase: To a 0.250 mL L-fucitol solution (100 mg/mL) were added 0.626 mL of water, followed by 0.050 mL of $K_2HPO_4/KH_2PO_4$ buffer, pH 7.0, 0.005 mL of peroxidase in water (7500 U/mL), 0.004 mL of catalase in water (724 200 U/mL), 0.065 mL of galactose oxidase (2705 U/mL in 100 mM $K_3PO_4$ buffer, pH 6.0). All reactions were purged with oxygen and stirred for 60 min. The course of the reaction was monitored by HPLC. The results of the various reactions are summarized in FIG. 3.

Example 3

Influence of L-fucitol Concentration on the Biocatalytic Oxidation of L-fucitol

Figure 2:
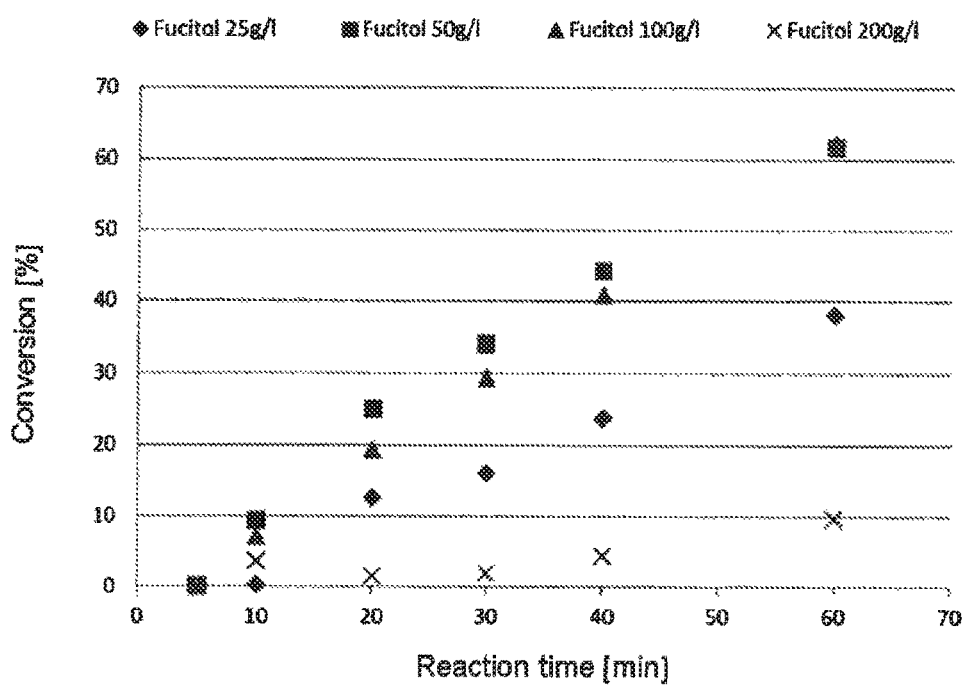
FIG. 2 (FIG. 2) shows the influence of substrate concentration on the conversion of L-fucitol to L-fucose using a galactose oxidase over time.

The following experiments were carried out on a 1.0 mL scale: 25 g/L L-fucitol: To a 0.100 mL L-fucitol solution (100 mg/mL) were added 0.231 mL of water, followed by 0.040 mL of K2HPO4/KH2PO4 buffer solution, pH 7.0, 0.005 mL of peroxidase in water (7500 U/mL), 0.004 mL of catalase in water (724 200 U/mL), 0.065 mL of galactose oxidase (2705 U/mL in 100 mM K3PO4 buffer, pH 6.0). 50 g/L L-fucitol: 0.020 g of L-fucitol were added to 0.281 mL of water, followed by 0.040 mL of K2HPO4/KH2PO4 buffer solution, pH 7.0, 0.004 mL of peroxidase in water (7500 U/mL), 0.0032 mL of catalase in water (724 200 U/mL), 0.052 mL of galactose oxidase (2705 U/mL in 100 mM K3PO4 buffer, pH 6.0). 100 g/L L-fucitol: 0.040 g of L-fucitol was added to 0.202 mL of water, followed by 0.040 mL of K2HPO4/KH2PO4 buffer solution, pH 7.0, 0.0080 mL of peroxidase in water (7500 U/mL), 0,0064 mL of catalase in water (724 200 U/mL), 0.104 mL of galactose oxidase (2705 U/mL in 100 mM K3PO4 buffer, pH 6.0). 200 g/L L-fucitol: 0.080 g of L-fucitol was added to 0.044 mL of water, followed by 0.040 mL of K2HPO4/KH2PO4 buffer solution, pH 7.0, 0.0160 mL of peroxidase in water (7500 U/mL), 0.0127 mL of catalase in water (724 200 U/mL), 0.207 mL of galactose oxidase (2705 U/mL in 100 mM K3PO4 buffer, pH 6.0). All reactions were purged with oxygen and stirred for 60 min. The course of the reaction was monitored by HPLC. The results are summarized in FIG. 2.

Figure 4:
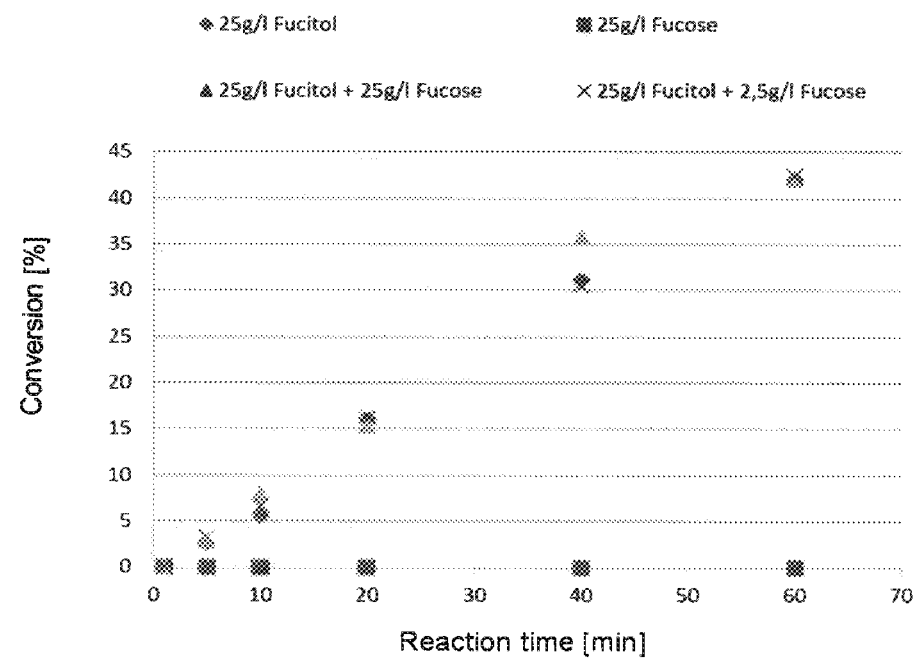
FIG. 4 (FIG. 4) shows the influence of L-fucose on the conversion of L-fucitol to L-fucose using a galactose oxidase over time.

FIG. 4 shows a further control experiment, in which additionally the influence of L-fucose on the conversion of L-fucitol was investigated.

Example 4

Fermentative Production and Recovery of Galactose Oxidase

Pichia pastoris was transformed with a suitable vector in which the wild type galactose oxidase gene of *Fusarium* spp. had been cloned. As vector, any available *Pichia* compatible vector proved useful. Additionally, different tags were used, either to assist the purification of the enzyme obtained and/or to effect the secretion thereof into the culture supernatant. A methanol-inducible promoter was selected as promoter. This showed that *Pichia* was suitable as host organism on the fermenter scale to induce the expression of large amounts of galactose oxidase. The galactose oxidase obtained was optionally isolated or recovered from the culture supernatant and optionally purified. The galactose oxidase recovered had an activity of about 3000 U/g. In the case of the use of a filamentous fungus as recombinant fungus, the secretion of the galactose oxidase was also effected directly into the culture supernatant.

Further examples with further expression strains comprising *E. coli* and various well-known fungus strains were made and the vectors, control elements, media and culture conditions used were adapted accordingly. These modifications are well known to those skilled in the art. All these expressions gave galactose oxidase in sufficient amount, purity and with sufficient activity to catalyze the biocatalytic production of L-fucose. Yeast and fungal strains have proven to be particularly preferred strains.

The invention claimed is:

1. A method for producing L-fucose, comprising the following steps:
   (a) providing L-fucitol, a galactose oxidase of the enzyme class EC 1.1.3.9, a peroxidase and a catalase,
   (b) combining L-fucitol, the galactose oxidase, the peroxidase, and the catalase to form a mixture,
   (c) incubating the resulting mixture under conditions permitting the biocatalytic oxidation of L-fucitol to L-fucose, and
   (d) optionally isolating the synthesized L-fucose.

2. The method according to claim 1, wherein step (b) comprises or consists of the following substeps:
   (b1) providing a recombinant microorganism or fungus for the recombinant expression of a galactose oxidase of the enzyme class EC 1.1.3.9, wherein the microorganism or fungus comprises a transgene which encodes a galactose oxidase from a fungus of the order of the Hypocreales
   (b2) culturing the recombinant microorganism under conditions which permit the synthesis of a galactose oxidase, and
   (b3) optionally isolating the synthesized galactose oxidase.

3. The method according to claim 2, wherein the recombinant microorganism or fungus is selected from the group consisting of *Escherichia coli* spp., *Bacillus* spp., *Saccharomycetes*, *Kluyveromyces* spp., *Aspergillus* spp., *Trichoderma* spp., and a fungus of the phylum Ascomycota.

4. The method according to claim 3, wherein the recombinant microorganism or fungus is selected from the group consisting of: a *Escherichia coli* spp. selected from the group consisting of *E. coli* BL21, *E. coli* MG1655, *E. coli* W3110 and descendants thereof; a *Bacillus* spp. selected from the group consisting of *Bacillus licheniformis*, *Bacillus subitilis*, *Bacillus amyloliquefaciens*, and descendants thereof; a *Saccharomycetes* selected from the group consisting of a *Saccharomycetes* selected from the group consisting of the genus *Saccharomyces*, the genus *Komagataella*, *Pichia pastoris*, and descendants thereof; a *Kluyveromyces* spp. selected from the group consisting *K lactis*, and descendants thereof; an *Aspergillus* spp. selected from the group consisting of *A. oryzae*, *A. nidulans*, *A. niger*, and descendants thereof; a *Trichoderma* spp. selected from the group consisting of *T reesei*, *T harzianum*, and descendants thereof; and a fungus of the phylum Ascomycota selected from the group consisting of *Myceliopthora thermophila*, and a descendant thereof.

5. The method according to claim 4, wherein the peroxidase is the peroxidase from horseradish (*Armoracia rusticana*).

6. The method according to claim 1, wherein the catalase is the catalase from cattle (*Bos taurus*).

7. The method according to claim 2, wherein the transgene encodes a galactose oxidase selected from the genus *Fusarium* or from the species *Fusarium oxysporum*.

8. The method according to claim 1, wherein the peroxidase is selected from a peroxidase of the group consisting of the enzyme class EC 1.11.1.7.

9. The method according to claim 1, wherein the catalase is selected from a catalase of the group consisting of the enzyme class EC 1.11.1.6.

10. The method according to claim 1, wherein the concentration of L-fucitol in the mixture at the start of the incubation in step (c) is in the range from 1 to 500 g/L.

11. The method according to claim 1, wherein the concentration of galactose oxidase in the mixture at the start of the incubation in step (c) is in the range from 0.005 to 6.25 g/L.

12. The method according to claim 1, wherein the concentration of peroxidase in the mixture at the start of the incubation in step (c) is in the range from 0 to 0.5 g/L.

13. The method according to claim 1, wherein the concentration of catalase in the mixture at the start of the incubation in step (c) is in the range from 0 to 0.4 g/L.

14. The method according to claim 1, wherein, at the start of the incubation in step (c),
   the concentration of L-fucitol in the mixture is in the range from 5 to 250 g/L,
   the concentration of galactose oxidase in the mixture is in the range from 0.005 to 3.2 g/L,
   the concentration of peroxidase in the mixture is in the range from 0 to 0.3 g/L, and
   the concentration of catalase in the mixture is in the range from 0 to 0.2 g/L.

15. The method according to claim 1, wherein, at the start of the incubation in step (c),
   the concentration of L-fucitol in the mixture is in the range from 20 to 1.25 g/L,
   the concentration of galactose oxidase in the mixture is in the range from 0.005 to 0.5 g/L,
   the concentration of peroxidase in the mixture is in the range from 0 to 0.15 g/L, and
   the concentration of catalase in the mixture is in the range from 0 to 0.1 g/L.

16. The method according to claim 1, wherein the concentration of peroxidase in the mixture at the start of the incubation in step (c) is in the range from 0 to 0.3 g/L.

17. The method according to claim 1, wherein the concentration of peroxidase in the mixture at the start of the incubation in step (c) is in the range from 0 to 0.15 g/L.

18. A method for producing L-fucose, comprising:
adding L-fucitol to a culture medium of a recombinant microorganism or fungus expressing a transgene(s) in functional form, and
culturing the mixture under conditions permitting the biocatalytic oxidation of L-fucitol to L-fucose,
wherein the recombinant microorganism or fungus comprises a transgene which encodes a galactose oxidase of the enzyme class EC 1.1.3.9 from a fungus of the genus *Fusarium*, and further comprises a transgene selected from a peroxidase selected from a peroxidase of the group consisting of the enzyme class EC 1.11.1.7, and a catalase selected from a catalase of the group consisting of the enzyme class EC 1.11.1.6, wherein the recombinant microorganism or fungus is selected from the group consisting of *Escherichia coli* spp., *Bacillus* spp., *Saccharomycetes, Kluyveromyces* spp., *Aspergillus* spp., *Trichoderma* spp., and a fungus of the phylum Ascomycota.

19. The method according to claim 18, wherein the recombinant microorganism or fungus is selected from the group consisting of: an *Escherichia coli* spp. selected from the group consisting of *E coli* BL21, *E. coli* MG1655, *E coli* W3110 and descendants thereof, a *Bacillus* spp, selected from the group consisting of *Bacillus licheniformis, Bacillus subitilis, Bacillus amyloliquefaciens*, and descendants thereof, a *Saccharomycetes* selected from the group consisting of the genus *Saccharomyces*, the genus *Komagataella, Pichia pastoris*, and descendants thereof, a *Kluyveromyces* spp. selected from the group consisting of *K lactis*, and descendants thereof an *Aspergillus* spp. selected from the group consisting of *A. oryzae, A. nidulans, A. niger*, and descendants thereof, a *Trichoderma* spp. selected from the group consisting of *T reesei, T harzianum*, and descendants thereof, and a fungus of the phylum Ascomycota selected from the group consisting of *Myceliopthora thermophila*, or a descendant thereof.

20. A method for the biocatalytic conversion of L-fucitol to L-fucose, comprising the following steps:
(a) providing a recombinant microorganism or fungus for the recombinant expression of a galactose oxidase, a peroxidase, and a catalase, wherein the microorganism comprises a transgene which encodes a galactose oxidase from a fungus of the genus *Fusarium*, a transgene which encodes a peroxidase, and a transgene with encodes a catalase, and wherein the recombinant microorganism or fungus is selected from the group consisting of: an *Escherichia coli* spp., a *Bacillus* spp., a *Saccharomycetes*, a *Kluyverormyces* spp., an *Aspergillus* spp., a *Trichoderma* spp., and a fungus of the phylum Ascomycota, or
(b1) providing a first recombinant microorganism or fungus for the recombinant expression of a galactose oxidase, wherein the microorganism or fungus comprises a transgene encoding a galactose oxidase from a fungus of the genus *Fusarium*;
(b2) providing a second recombinant microorganism or fungus for the recombinant expression of a peroxidase, wherein the microorganism or fungus comprises a transgene encoding a peroxidase selected from a peroxidase of the group consisting of the enzyme class EC 1.11.1.7; and
(b3) providing a third recombinant microorganism or fungus for the recombinant expression of a catalase, wherein the microorganism or fungus comprises a transgene encoding a catalase selected from a catalase of the group consisting of the enzyme class EC 1.11.1.6;
(c) culturing the recombinant microorganism and/or fungus under suitable conditions which permits the synthesis of the galactose oxidase, the peroxidase and the catalase,
(d) optionally isolating the synthesized galactose oxidase and the peroxidase and/or the catalase;
(e) combining L-fucitol, the galactose oxidase, the peroxidase, and the catalase to form a mixture; and
(f) incubating the resulting mixture under conditions permitting the biocatalytic oxidation of L-fucitol to L-fucose.

21. The method according to claim 20, wherein the recombinant microorganism or fungus of (a) is selected from the group consisting of: an *Escherichia coli* spp. selected from the group consisting of *E. coil* bL21, *E.coli* MG1655, *E. coli* W3110 and descendants thereof; a *Bacillus* spp. selected from the group consisting of *Bacillus licheniformis, Bacillus subitilis, Bacillus amyloliquefaciens*, and descendants thereof; a *Saccharomycetes* selected from the group consisting of a *Saccharomycetes* selected from the group consisting of the genus *Saccharomyces*, the genus *Komagataella, Pichia pastoris*, and descendants thereof; a *Kluyveromyces* spp. selected from the group consisting *K lactis*, and descendants thereof; an *Aspergillus* spp. selected from the group consisting of *A. oryzae, A. nidulans, A. niger*, and descendants thereof; a *Trichoderma* spp. selected from the group consisting of *T. reesei, T harzianurn*, and descendants thereof; and a fungus of the phylum Ascomycota selected from the group consisting of *Myceliopthora thermophila*, and a descendant thereof.

22. The method according to claim 20, wherein the second recombinant microorganism or fungus comprises a transgene encoding the peroxidase from horseradish (*Armoracia rusticana*); and the third recombinant microorganism or fungus comprises a transgene encoding the catalase from cattle (*Bos taurus*).

* * * * *